United States Patent
Sprunck et al.

(10) Patent No.: US 6,949,693 B2
(45) Date of Patent: Sep. 27, 2005

(54) PROMOTERS FOR GENE EXPRESSION IN CARYOPSES OF PLANTS

(75) Inventors: Stefanie Sprunck, Hamburg (DE); Antje Kluth, Hamburg (DE); Dirk Becker, Hamburg (DE); Stephanie Luetticke, Hamburg (DE); Horst Loerz, Hamburg (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 197 days.

(21) Appl. No.: 09/899,718

(22) Filed: Jul. 5, 2001

(65) Prior Publication Data

US 2003/0046731 A1 Mar. 6, 2003

(30) Foreign Application Priority Data

Jul. 6, 2000 (DE) .......................................... 100 32 379
Aug. 26, 2000 (DE) .......................................... 100 41 861

(51) Int. Cl.$^7$ .......................... C12N 15/00; C12N 15/11; C12N 15/82; A01H 5/00; A01H 5/02
(52) U.S. Cl. ........................ 800/287; 800/278; 800/298; 435/320.1; 435/419; 536/24.1
(58) Field of Search .............................. 435/320.1, 419; 800/287, 298, 278; 536/24.1

(56) References Cited

PUBLICATIONS

Visser et al., Expression of a chimaeric–bound starch synthase–GUS gene in transgenic potato plants, 1991, Plant Molecular Biology, vol. 17, pp. 691–699.*

Steege et al., Potato granule–bound starch synthase promoter–controlled GUS expression: regulation of expression after transient and stable transformation, 1992, Plant Molecular Biology, vol. 20, pp. 19–30.*

Far et al., Concepts to automate the theoretical design of effective antisense oligonucleotides, 2001, Bioinformatics, vol. 17, pp. 1058–1061.*

Plant Molecular Biology 22, 67–82, 1993, Ainsworth et al, Expression, Organisation and Structure of the genes encoding the Waxy Protein (granule–bound starch synthase) in Wheat.

Block, Martina, Isolierung, Charakterisierung and Expressionsanalysen von Stärkesynthase–Genen aus Weizen (*Triticum aestivum* L.).

AB 008794, Mol. Biol. Evol. 15, (8), 978–987, (1998).

AB 008795, Mol. Biol. Evol. 15 (8), 978–987 (1998).

AJ 006294 "Antirrhinum majus promoter for waxy gene".

X07931 "Barley DNA for waxy locus encoding starch synthase", Nucleic Acids Research, 16, (14B), 7185–7186 (1988).

Mol. Gen. Genet (1991), 228; 240–248, van der Leij et al, "Sequence of the Structural Gene for Granule–bound Starch Synthase of Potato (*Solanum tuberosum* L.) and Evidence for a Single Point Deletion in the amf allele".

Mol. Gen. Genet. (1986), 203; 237–244, Klösgen et al, "Molecular Analysis of the Waxy Locus of *Zea Mays*".

X58453, Potato Gene for Granule–Bound Starch Synthase; Mol. Gen. Genet 228, (1–2), 240–248 (1991); Plant Mol. Biol. 20 (1), 19–30, (1992); Plant J. 10 (6), 981–991, (1996).

Nucleic Acids Research, vol. 16, No. 14, 1988, Structural Analysis of the waxy Locus from *Hordeum vulgare*, Rohde et al, Accession Nos. X07931, X07932; pp. 7185–7186.

Plant Molecular Biology 16, 1099–1101, 1991, Clark et al, "Nucleic Sequence of a Wheat (*Triticum aestivum* L.) cDNA Clone Encoding the Waxy Protein".

Plant Molecular Biology 20, 19–30, 1992, van der Steege et al, Potato Granule–Bound Starch Synthase Promoter–Controlled GUS Expression: Regulation of Expression After Transient and Stable Transformation.

Hirano et al, pp. 978–987, "A Single Base Change Altered the Regulation of the Waxy Gene at the Posttranscriptional Level During the Domestication of Rice".

* cited by examiner

*Primary Examiner*—David Guyo
*Assistant Examiner*—Daniel M. Sullivan
(74) *Attorney, Agent, or Firm*—Frommer Lawrence & Haug LLP

(57) ABSTRACT

The present invention relates to promoters which permit a caryopsis-specific expression or suppression of genes in genetically modified plants, to methods for the tissue-specific gene expression or gene suppression in plants, expression cassettes, recombinant vectors and host cells containing such promoters, to transgenic plant cells and plants transformed with said promoters, and to methods for generating such plant cells and plants.

15 Claims, No Drawings

PROMOTERS FOR GENE EXPRESSION IN CARYOPSES OF PLANTS

The present invention relates to promoters which permit a caryopsis-specific expression or suppression of genes in genetically modified plants, to methods for the tissue-specific gene expression or gene suppression in plants, expression cassettes, recombinant vectors and host cells containing such promoters, to transgenic plant cells and plants transformed with said promoters, and to methods for generating such plant cells and plants.

Prior-art documents whose disclosure is herewith incorporated into the present application by reference are cited hereinbelow.

The application of plants whose genetic material has been modified with the aid of genetic engineering methods has proved advantageous in many fields of agriculture in order to transfer certain characteristics to crop plants. The predominant aims are in particular crop protection, but also improved quality and yield of the harvestable products.

A large number of methods for genetically modifying dicotyledonous and monocotyledonous plants are known (cf., inter alia, Gasser and Fraley, Science 244 (1989), 1293–1299; Potrykus, Ann. Rev. Plant Mol. Biol. Plant Physiol. 42 (1991), 205–225). They are frequently based on the transfer of gene constructs which, in most cases, constitute combinations of specific coding regions of structural genes with promoter regions of the same or other structural genes, and transcription terminators.

In connection with the expression of structural genes, providing promoters is of great importance for generating transgenic plants, since the specificity of a promoter is decisive for the point in time at which, the tissue types in which, the physiological conditions under which and the intensity with which a transferred gene is expressed in the modified plant.

Transcriptional initiation and regulation is subject to the DNA segment of a gene termed promoter. As a rule, promoter sequences are in the 5'-flanking region of a transcribed gene. Under certain circumstances, individual elements of a promoter (for example transcriptional enhancers) can also be located in the 3'-flanking region or within intron sequences (Kuhlemeier (1992) Plant Mol. Biol. 19: 1–14; Luehrsen (1994) The Maize Handbook, 636–638).

A large number of promoters capable of governing the expression of transferred genes or structural genes in plants is already known. The most frequently used promoter is the 35S CaMV promoter (Franck et al., Cell 1 (1980), 285–294), which leads to constitutive expression of the gene introduced.

Frequently, inducible promoters are also employed, for example for wound induction (DE-A-3843628), chemical induction (Ward et al., Plant Molec. Biol. 22 (1993), 361–366) or light induction (Fluhr et al., Science 232 (1986), 1106–1112).

The use of cell- and tissue-specific promoters has also been described: stomata-specific gene expression (DE-A4207358), seed-, tuber- and fruit-specific gene expression (reviewed in Edwards and Coruzzi, Annu. Rev. Genet. 24 (1990), 275–303; DE-A-3843627), phloem-specific gene expression (Schmülling et al., Plant Cell 1 (1989), 665–470), root-nodule-specific gene expression (DE-A-3702497) or meristem-specific gene expression (Ito et al., Plant Mol. Biol. 24 (1994), 863–878).

The use of the promoters described frequently entails disadvantages. Promoters which bring about a constitutive expression of the genes controlled by them can be employed, for example, for generating herbicide-tolerant and pathogen-resistant plants, but have the disadvantage that the products of the genes controlled by them are present in all parts of the plant, which may be undesirable, for example when the plants are intended for consumption. A negative aspect of tissue- and/or development-independent expression of a transgene can also be an undesired effect on plant development. Inducible promoters likewise entail disadvantages, since the induction conditions are typically difficult to control in the open in the case of agricultural plants.

For managing different approaches of the genetic modification of plants, it is, in addition, necessary to place genes to be regulated differentially under the control of various promoters. It is therefore necessary to provide various promoter systems with differing specificities.

For example, the controlled expression of transgenes is very useful for introducing resistance properties into plants or modifying metabolic procedures in plants. If a transgene is to engage in defined metabolic pathways of a plant, for example if it is to produce a novel constituent or to protect against attack by pathogens, its space- and/or time-controlled expression is only possible when using an inducible and/or tissue- and/or development-specific promoter. Only this makes possible the targeted production of desired constituents in a defined developmental stage or tissue of the plant. For example, the use of tissue- and/or development-specific promoters may be advantageous over a tissue- and/or development-independent expression for the application of antisense technology, where the expression of homologous genes is to be prevented: thus, the antisense effect takes place precisely at the developmental stage at which, or in the tissue of the plant or in which, the homologous gene is also expressed.

Only a limited number of promoters which regulate gene expression in the caryopsis are known as yet. The management of certain approaches in the genetic modification of plants require the provision of alternative promoter systems for gene expression in the caryopsis whose regulation differs from that of the known systems.

Starch biosynthesis genes whose gene products are expressed specifically in the storage tissue of the caryopsis, but not in vegetative tissues, have been isolated from various plant species, for example the relevant genes or cDNA clones of GBSS I. They include the waxy locus from maize (Klösgen et al. (1986) Mol. Gen. Genet. 203: 237–244), and barley (Rohde et al. (1988) Nucleic Acid Research 16, No. 14: 7185–7186), rice (Wang et al. (1990) Nucleic Acid Research 18: 5898), potato (van der Leij et al. (1991) Mol. Gen. Genet. 228: 240–248), pea (Dry et al. (1992) Plant J. 2: 193–202), millet (Salehuzzaman et al. (1993) Plant Mol. Biol. 20: 947–962), Hirse (Hsingh et al. (1995) Acc. No. U23954) and sugar beet (Schneider et al. (1999) Mol. Gen. Genet. 262: 515–524).

A wheat waxy cDNA has also been isolated and sequenced (Clark et al. (1991) Plant Mol. Biol. 16: 1099–1101; Ainsworth et al. (1993) Plant Mol. Biol. 22: 67–82). Another GBSS I clone has been isolated from a cDNA library of approx. 20 day old wheat caryopses (Block (1997) "Isolierung, Charakterisierung und Expressionsanalysen von Stärkesynthase-Genen aus wheat" [Isolation, characterization and expression analyses of wheat starch synthase genes] (*Triticum aestivum* L.), PhD thesis, University of Hamburg). It was confirmed that this GBSS I is expressed in the caryopsis and in pollen.

While three homologous waxy structural genes positioned on chromosomes 7A, 4A and 7D of hexaploid wheat have been isolated in the meantime (Murai et al. (1999)

Gene 234: 71–79), the promoter sequences of these or other genomic clones from wheat remain unknown. Only the 5'-flanking regions of GBSS I from barley (Genlibrary Acc.No. X07931), antirrhinum (Genlibrary Acc.No. AJ006294), rice (Genlibrary Acc.No. AB008794, AB008795), potato (Genlibrary Acc.No. X58453) and maize (Genlibrary Acc.No. X03935) are known.

A cDNA clone of a starch-globule-band type II starch synthase (GBSS II) which is expressed not in the endosperm but only in the leaves and the pericarp of wheat has recently been isolated (Vrinten & Nakamura (2000) Plant Physiol. 122: 255–263). In diploid wheat (*Triticum monococcum* L.), a 56 kDa isoform of a GBSS has also been described at the protein level (Fujita & Taira (1998) Planta 207: 125–132). This isoform can be detected in the pericarp, the aleuron and the embryo of immature caryopses.

The aim of the present invention is thus to provide means for making possible a targeted caryopsis-specific gene expression in genetically modified plants, preferably in monocots.

The use of the means according to the invention, i.e. the nucleic acid molecules, vectors, cells or plants according to the invention, makes it possible to engage, in a tissue- and/or development-specifically defined manner, in the plant's metabolism, for example in the biosynthesis of storage starch or the utilization of the caryopsis as storage or synthesis organ for starch and other reserve substances (for example polyglucans, fatty acids, modified or unmodified storage proteins or biopolymers).

Thus, genes can be expressed specifically and at an early point in time in the caryopsis under the control of the promoter sequences according to the invention, in particular during the grain development of cereals.

Moreover, genes can be suppressed specifically and at an early point in time in the caryopsis by what are known as gene silencing strategies (cosuppression) by means of the promoter sequences according to the invention, in particular during the grain development of cereals. Cosuppression strategies using promoters have been described in detail by Vaucheret et al. (Vaucheret et al., 1998, 16(6), 651–659). The section "Transcriptional trans-inactivation" on page 652 of the paper by Vaucheret et al., which specifically describes cosuppression strategies for which the promoters according to the invention are suitable, in particular those which can be termed "ectopic trans-inactivation" therein (Matzke et al., 1994, Mol. Gen. Genet. 244, 219–229), be herewith incorporated into the present application by reference. Thus, the promoters according to the invention can be used to suppress gene expression of any genes which are under the control of a promoter which is accessible as target for cosuppression by the promoters according to the invention. If appropriate, even a sequence segment of as little as approximately 90 bp in length suffices for this purpose.

The promoters according to the invention thus make possible, for example, the targeted modification of storage starch: to make possible the widest possible application of starch for a very wide range of industrial requirements, it is desirable to provide plants which are capable of synthesizing starches with defined properties. Thus, decisive properties such as solubility, gelatinization behavior, tendency to undergo retrogradation, viscosity and complex formation are determined by the amylose/amylopectin ratio, the degree of branching of the amylopectin and the derivatization of the polymers. A targeted modification of such properties replaces complicated methods for separating amylose and amylopectin or the expensive chemical modification of starch.

A limited possibility of obtaining such plants is the application of traditional plant breeding methods. Thus, an amylose-free "waxy" wheat was generated successfully by hybridizing spontaneously occurring mutants (Nakamura et al. (1995) Mol. Gen. Genet. 248: 253–259). Owing to the polyploid character of the commercially important aestivum wheat, mutations relating to the starch structure are not easily recognized since they are compensated for by intact alleles. Thus, the application of traditional plant breeding methods is difficult. Moreover, only enzyme activities which already exist can be resorted to. Novel activities which have hitherto not been identified in plants or which have been identified in plants (or other organisms) which cannot be hybridized with the target plant can also not be improved with the aid of plant breeding methods.

An alternative is the targeted modification of starch-producing plants by genetic engineering methods. However, prerequisite herefor is, besides the identification and isolation of genes whose gene products are involved in starch synthesis and/or of starch modification, the use of specific promoters which may be a tissue- and/or development-specific expression of the genes controlled by them in the starch-forming tissues.

Employing the promoter sequences according to the invention also additionally makes possible the introduction of those genes which impart, to the cereal endosperm, a modified function as storage tissue for other reserves.

These aims are achieved in accordance with the invention by providing the use forms characterized in the patent claims.

It has now been found that a promoter as defined hereinbelow surprisingly brings about, in plants, a caryopsis-specific expression of a coding nucleotide sequence controlled by this promoter.

Thus, the present invention relates to a nucleic acid molecule with the function of a caryopsis-specific promoter, which nucleic acid molecule a) comprises the nucleic acid sequence defined by Seq ID No. 1 or deposited by DSM 13398 (plasmid p. 11/1);

b) comprises one or more sequence elements selected from the group consisting of i) cacgcaaagg cgcgtcggcc agccacgac (Seq ID No. 2);

ii) agaaacaaac aaacaaacaa aaaagt (Seq ID No. 3);

iii) cctttcagga cgatgcttcg gtgccttaag acacctacc tttgtgtcta tgacatgtga gcccaacag atggct (Seq ID No. 4);

iv) cccgtctagg cgttcggtgt ccggcc (Seq ID No. 5);

v) cagggagcct tcga (Seq ID No. 6);

vi) tcagccagtt ccaccccgtg cacg (Seq ID No. 7) and vii) tactctggtc atgttaa (Seq ID No. 8);

c) comprises a functional portion of the nucleic acid sequence stated under a);

d) comprises a sequence which hybridizes with at least one of the nucleic acid sequences stated under a) and/or b); and/or e) comprises a sequence which has at least 60% identity, preferably at least 75% identity, in particular at least 90% identity and very especially preferably at least 95% identity, with one of the nucleic acid sequences stated under a).

The subject matter of the present invention is furthermore a nucleic acid molecule with the function of a caryopsis-specific promoter which a) comprises one or more sequence elements selected from the group consisting of i) cacgcaaagg cgcgtcggcc agccacgac (Seq ID No. 2);
ii) agaaacaaac aaacaaacaa aaaagt (Seq ID No. 3);
iii) cctttcagga cgatgcttcg gtgccttaag acacctacc tttgtgtcta tgacatgtga gcccaacag atggct (Seq ID No. 4);
iv) cccgtctagg cgttcggtgt ccggcc (Seq ID No. 5);
v) cagggagcct tcga (Seq ID No. 6);
vi) tcagccagtt ccaccccgtg cacg (Seq ID No. 7) and
vii) tactctggtc atgttaa (Seq ID No. 8) and
b) comprises a functional portion of Seq ID No. 1, preferably one or more sequence elements from the group consisting of nucleotides of positions 1–26; 31–62; 68–103; 109–140; 146–240; 247–255; 260–263; 283–294; 315–329; 337–408; 414–450; 457–500; 506–519; 524–558; 568–609; 620–638; 645–655; 661–701; 728–752; 758–770; 776–792; 802–821; 827–869; 875–889; 896–928; 957–965; 974–986; 1032–1037; 1074–1106; 1114–1139; 1145–1258; 1274–1288; 1294–1323; 1330–1343; 1355–1362; 1369–1398; 1409–1448; 1454–1485; 1496–1557; 1577–1602; 1610–1643; 1663–1689; 1696–1747; 1755–1835; 1843–1870; 1876–1886; 1902–1929; 1938–1987; 1994–2013; 2020–2034; 2041–2076; 2084–2137; 2138–2298; 2148–2241; 2251–2282; 2298–2317; 2317–3139; 2335–2378; 2425–2487; 2495–2522; 2528–2553; 2560–2656; 2663–2706; 2712–2811; 2824–2841; 2853–2867; 2885–2922; 2928–2943; 2951–2983; 2990–3021; 3036–3139 and 3051–3139 of Seq. ID No. 1.

The terms "nucleic acid molecule according to the invention" and "promoter according to the invention" are generally used synonymously for the purposes of the present invention.

In a preferred embodiment, the promoters according to the invention are those of plant genes, preferably monocots, or derived therefrom. In a further, preferred embodiment, the promoters according to the invention are suitable for expressing or suppressing genes in genetically modified plants, preferably in monocots, in particular for the expression or suppression of starch synthase genes. In this context, the promoters according to the invention can be derived from plant genes, modified by recombinant DNA techniques and/or generated synthetically.

The promoters according to the invention can be modified for example by being combined with further cis-regulatory elements. Thus, the promoters according to the invention can additionally be combined with enhancer elements in order to enhance the expression of the corresponding nucleic acid molecule without however influencing its tissue-specific expression. Individual cis-elements (see below) of the isolated promoters can also be combined with each other to give regulatory units.

In the context of the present invention, a "promoter" is to be understood as meaning a DNA sequence comprising the regulatory portion of a gene, preferably a structural gene. "Regulatory portion" of a gene is to be understood as meaning that portion that determines the expression conditions of the gene. A regulatory portion has a sequence motif with which transcriptional factors and RNA polymerase interact and initiate transcription of the coding portion of the gene. In addition, the regulatory portion can comprise one or more positive regulatory elements, known as enhancers. Additionally or instead, however, it may also comprise negatively regulatory elements, known as silencers. A "structural gene" is generally to be understood as meaning a genetic unit of regulatory and coding portions whose gene product is generally a protein. The information for the primary amino acid sequence of the gene product is present in the coding portion of the structural gene, while the regulatory portion determines when, in what tissues, under what physiological conditions and in what quantities the transcript of the coding portion is formed according to whose template the gene product is synthesized.

The term "caryopsis-specific" is to be understood as meaning, for the purposes of the present invention, that a gene under the control of a promoter according to the invention is expressed in the caryopsis, i.e. endosperm, pericarp and scutellum and/or pollen, preferably at an early point in time after fertilization, i.e. approximately 15–5 dap (dap=days after pollination), preferably approximately 10–5 dap, in particular approximately 5 dap. In particular, caryopsis specificity for the purposes of the present invention exists when the promoter according to the invention favors the expression of a gene in the caryopsis over other tissues such as, for example, mature leaves or roots and brings about a significant increase in the caryopsis, i.e. an expression rate which is increased by a factor of 2 to 5, preferably 5 to 10, in particular 10 to 100.

In the context of the present invention, caryopsis specificity can be analyzed for example by customary reporter gene experiments. To test an isolated promoter sequence for its promoter activity in the caryopsis, the promoter can, for example, be linked operably to a reporter gene, such as, for example, *E. coli* β-glucuronidase gene (gus) in an expression cassette or in a vector for plant transformation. This construct is then used for transforming plants. The β-glucuronidase (GUS) expression in the caryopsis is then determined in comparison with other tissues such as, for example, mature leaves or roots, for example as described by Martin et al. (The GUS Reporter System as a Tool to Study Plant Gene Expression, In: GUS Protocols: Using the GUS genes as a Reporter of Gene Expression, Academic Press (1992), 23–43).

The skilled worker is familiar with the term "caryopsis"; it comprises in particular pericarp and endosperm. Since these tissues undergo dynamic development, the development of the endosperm, for example, into various types of cells and tissues correlates with different biochemical activities, owing to differential gene expression. Additional reference may be made to Olsen et al. (Olsen et al., 1999, Trends in Plant Science 4 (7), 253–257).

The promoter according to the invention permits caryopsis-specific gene expression of a coding nucleotide sequence controlled by it. It constitutes an interesting alternative to known promoters since it is also capable of mediating the gene expression in the pericarp and, additionally, since it is active in the caryopsis already at a very early point in time, i.e. approximately 15–5 dap, preferably approximately 10–5 dap, in particular approximately around 5 dap. The promoter according to the invention allows in particular the expression of those genes whose gene products are involved in the starch metabolism of monocots, in particular wheat, to be governed efficiently.

The promoters according to the invention can be used in many different ways. For example, they make possible the generation of transgenic plants which, owing to a modified metabolism in the caryopsis, show a qualitatively and/or quantitatively modified composition of reserves in their storage tissue, i.e. in the cereal grain.

Besides a promoter which exhibits the entire sequence defined by SEQ ID No. 1 or the sequence deposited accordingly by DSM 13398, the present invention also relates to promoters which exhibit a functional portion of this sequence and which, in plants, bring about a caryopsis-specific expression of a coding nucleotide sequence controlled by them.

A "functional portion" of the promoter according to the invention is to be understood as meaning, for the purposes of the present invention, those sequences which do not comprise the complete sequences of said promoters, as defined by SEQ ID No. 1 or deposited by DSM 13398, but which are truncated. Despite the truncation, "functional portions" have the caryopsis specificity according to the invention.

Sequences comprising a functional portion of Seq. ID No. 1 preferably exhibit one or more of the segments from SEQ ID No. 1 enumerated hereinbelow: 1–26; 31–62; 68–103; 109–140; 146–240; 247–255; 260–263; 283–294; 315–329; 337–408; 414–450; 457–500; 506–519; 524–558; 568–609; 620–638; 645–655; 661–701; 728–752; 758–770; 776–792; 802–821; 827–869; 875–889; 896–928; 957–965; 974–986; 1032–1037; 1074–1106; 1114–1139; 1145–1258; 1274–1288; 1294–1323; 1330–1343; 1355–1362; 1369–1398; 1409–1448; 1454–1485; 1496–1557; 1577–1602; 1610–1643; 1663–1689; 1696–1747; 1755–1835; 1843–1870; 1876–1886; 1902–1929; 1938–1987; 1994–2013; 2020–2034; 2041–2076; 2084–2137; 2138–2298; 2148–2241; 2251–2282; 2298–2317; 2317–3139; 2335–2378; 2425–2487; 2495–2522; 2528–2553; 2560–2656; 2663–2706; 2712–2811; 2824–2841; 2853–2867; 2885–2922; 2928–2943; 2951–2983; 2990–3021; 3036–3139 and/or 3051–3139; the nucleotide positions are based on SEQ ID No. 1. "Functional portions" of the promoter according to the invention preferably have a length of approximately 50–3100 bp, in particular approximately 100–3100 bp and very especially approximately 430–3100 bp.

A measure for the promoter activity is, for example, the expression rate determined for a particular marker gene when under the regulatory control of the promoter according to the invention. Examples of suitable marker genes are the *E. coli* β-glucuronidase gene (gus) (Jefferson (1987) Plant Molecular Biology Reporter Vol. 5 (4): 387–405) or the green fluorescence protein gene (gfp) (Baulcombe et al., Plant J. 7 (16) (1993), 1045–1053). The organ or tissue specificity can be determined readily by comparison of the expression rates for said marker genes determined from individual tissues or organs of the plant. Functional portions of the promoter sequences comprise, for the purposes of the present invention, naturally occurring variants of the sequences according to the invention and also artificial nucleotide sequences, for example those obtained by chemical synthesis.

A "functional portion" is to be understood as meaning in particular also natural or artificial mutations of an originally isolated promoter sequence which have the abovementioned physiological functions and features according to the invention.

The term "mutations" encompasses substitutions, additions, deletions, exchanges and/or insertions of one or more nucleotides, in particular of suitable cis-elements, specifically as defined hereinbelow (see below). Thus, the scope of the present invention also extends for example to those nucleotide sequences which can be obtained by modifying the promoter sequence defined by Seq ID No. 1 or the promoter sequence deposited by DSM 13398. The aim of such a modification can be, for example, the generation of fragments or the insertion or repositioning of known nucleotide motifs such as, for example, restriction cleavage sites or cis-elements.

Functional portions of the promoter sequence according to the invention in this context also comprise those promoter variants whose promoter activity is reduced or enhanced compared with the unmodified promoter (wild type).

In particular, functional portions of the promoter sequences according to the invention are the regions identifiable by deletion analysis (cf. examples part), preferably the sequence segments 948–3139; 1006–3139; 1240–3139; 1259–3139; 1382–3139; 1486–3139; 1514–3139; 1655–3139; 1822–3139; 1887–3139; 2138–3139 and 2176–3139 of Seq ID No. 1.

In principle, the activity of a eukaryotic RNA polymerase II promoter is caused by the synergistic action of various trans-active factors (DNA-binding molecules such as proteins or hormones) which bind to the various cis-regulatory DNA elements present in the promoter, generally in a region approximately 10–20 nucleotides in length. These factors interact directly or indirectly with one or more factors of the basic transcription machinery, which eventually leads to the formation of a pre-initiation complex in the vicinity of the transcription start (Drapkin et al., Current Opinion in Cell Biology 5 (1993), 469–476). A module-light construction of the eukaryotic RNA polymerase II promoters can be assumed where the cis-elements (modules), as components of the promoter, specifically determine its activity (Tjian and Maniatis, Cell 77 (1994), 5–8).

Individual subdomains of the promoter according to the invention which potentially mediate tissue specificity can be identified for example by fusion with a minimal promoter/reporter gene cassette. A minimal promoter is to be understood as meaning a DNA sequence comprising a TATA-box located approximately 20 to 30 base pairs upstream of the transcription start, or an initiator sequence (Smale and Baltimore, Cell 57 (1989), 103–113; Zawel and Reinberg, Proc. Natl. Acad. Sci. 44 (1993), 67–108; Conaway and Conaway, Annu. Rev. Biochem 62 (1993), 161–190). Examples of minimal promoters are the −63 to +8 Δ35S promoter (Frohberg, PhD thesis at the FU Berlin FB Biologie (1994)), the −332 to +14 minimal patatin class I promoter, and the −176 to +4 minimal PetE promoter (Pwee et al., Plant J. 3 (1993), 437–449).

Moreover, subdomains or cis-elements of the promoter according to the invention can also be identified via deletion analyses or mutageneses (Kawagoe et al., Plant J. 5(6) (1994), 885–890). The test for functionality of such a subdomain or cis-elements of the promoter can be effected in planta by detecting reporter gene activity in stably transformed cells.

In a further embodiment, the present invention therefore relates to modifications of SEQ ID No. 1 obtained in particular by the di- or multimerization of subdomains or cis-elements of SEQ ID No. 1.

In a further embodiment of the invention, an increased promoter activity compared with the wildtype is achieved by combining the promoter according to the invention with what is known as an enhancer.

Various enhancers have been described in the literature, all of which generally bring about an increase in the expression in a tissue-specific manner, the tissue specificity generally being determined by the particular enhancer used (Benfey et al., Science 250 (1990), 959–966; Benfey et al., EMBO J. 8 (1989), 2195–2202; Chen et al., EMBO J. 7, (1988), 297–302; Simpson et al., Nature 323 (1986), 551–554).

In addition, there are also enhancers such as, for example, the PetE enhancer (Sandhu et al., Plant Mol. Biol. 37 (1998), 885–896), which do not act in a tissue-specific manner and which can therefore be placed before the promoter according to the invention as quantitative enhancer elements in order to increase expression in the caryopsis without modifying the quality or tissue specificity of the promoter according to the invention.

Furthermore, synthetic enhancers can also be used; these are, for example, derived from naturally occurring enhancers and/or are obtained by combining various enhancers.

Likewise, the present invention also relates to promoters which exhibit a nucleotide sequence which hybridizes with the nucleotide sequence defined by SEQ ID No. 1 or deposited by DSM 13398, preferably under stringent conditions, and which promoters exert, in plants, a caryopsis-specific effect on the expression of a coding nucleotide sequence controlled by them.

In this context, the term "stringent conditions" means for example hybridization conditions as they are described in Sambrook et al. (Molecular Cloning, A Laboratory Manual, 2nd Edition (1989), Cold Spring Harbor Laboratory Press, Cold Spring Harbor, N.Y.). In particular, stringent hybridization takes place under the following conditions:

Hybridization buffer: 2×SSC; 10×Denhardt's solution (Ficoll 400+PEG+BSA; ratio 1:1:1); 0.1% SDS; 5 mM EDTA; 50 mM $Na_2HPO_4$; 250 μg/ml herring sperm-DNA; 50 μg/ml tRNA; or 0.25 M sodium phosphate buffer pH 7.2, 1 mM EDTA, 7% SDS Hybridization temperature T=65 to 68° C.;
Wash buffer 0.2×SSC; 0.1% SDS;
Wash temperature T=65 to 68° C.

Such promoters preferably have a sequence identity of at least 30%, preferably of at least 40%, preferably of at least 50%, especially preferably of at least 60%, particularly preferably of at least 70% and advantageously of at least 80%, preferably at least 90% and particularly preferably at least 95%, with the promoter sequence shown under SEQ ID No. 1 or portions thereof. The sequence identity of such promoter sequences is preferably determined by comparison with the nucleotide sequence shown under SEQ ID No. 1. When two sequences to be compared differ in length, the sequence identity preferably refers to the percentage of the nucleotide residues of the shorter sequence, which are identical to the nucleotide residues of the longer sequence. The sequence identity can be determined for example by using computer programs such as the Bestfit program (Wisconsin Sequence Analysis Package, Version 8 for Unix, Genetics Computer Group, University Research Park, 575 Science Drive Madison, Wis. 53711). Bestfit exploits the local homology algorithm of Smith and Waterman, Advances in Applied Mathematics 2 (1981), 482–489, to identify the segment with the highest sequence identity between two sequences. When applying Bestfit or another sequence alignment program to determine whether a particular sequence has, for example, 95% identity with a reference sequence of the present invention, the parameters are preferably set in such a way that the percentage identity over the entire length of the reference sequence is calculated and that homology gaps of up to 5% of the total number of nucleotides in the reference sequence are permitted. When using Bestfit, the so-called optional parameters can be left at their default values. The deviations which occur when comparing a given sequence with the above-described sequences of the invention can have been caused for example by addition, deletion, substitution, insertion or recombination. Promoter sequences which, as described above, hybridize with the nucleotide sequence defined by SEQ ID No. 1 or deposited by DSM 13398 are preferably derived from plant organisms, preferably from higher plants, especially preferably from monocots, particularly preferably from Gramineae, very especially plants of the genus *Triticum*.

Furthermore, the present invention also relates to promoters which exhibit a functional portion of the promoters according to the invention and which, in plants, bring about a caryopsis-specific expression of a coding nucleotide sequence controlled by them and which comprise one or more sequences of SEQ ID No. 2–SEQ ID No. 8.

In an especially preferred embodiment of the invention, the promoter according to the invention exhibits all of SEQ ID No. 1 or a functional portion of the nucleotide sequence defined by SEQ ID No. 1 or deposited by DSM 13398, in particular nucleotides 948–3139; 1006–3139; 1240–3139; 1259–3139; 1382–3139; 1486–3139; 1514–3139; 1655–3139; 1822–3139; 1887–3139; 2138–3139 and 2176–3139 from SEQ ID No. 1.

The present invention furthermore relates to expression cassettes comprising one or more promoters according to the invention. In this context, the term "expression cassette" is to be understood as meaning the combination of a promoter according to the invention with a nucleic acid sequence to be expressed. This nucleic acid sequence can be, for example, a polypeptide-encoding sequence, for example a gene which can be linked to the promoter in sense or antisense orientation. The nucleic acid sequence can also code a nontranslatable RNA, for example an antisense RNA or a ribozyme. These nucleic acid sequences can be used in conjunction with the promoter according to the invention to generate plants with a modified phenotype.

Furthermore, the expression cassettes according to the invention can comprise a transcription termination sequence downstream of the 3' end of the nucleic acid sequence which is linked to the promoter. In this context, a "transcription termination sequence" is to be understood as meaning a DNA sequence which is located at the 3' end of a coding gene segment and which is capable of bringing about transcription termination and, if appropriate, the synthesis of a poly-A tail. An example of such a termination sequence is that of the octopine synthase gene. The field worker is familiar with others.

Moreover, the present invention relates to vectors comprising at least one promoter according to the invention.

In an embodiment which is furthermore preferred, the promoter according to the invention in such a vector is linked to restriction cleavage sites or a polylinker, either of which permits integration of any sequences downstream of the promoter. In this context, a "polylinker" is to be understood as meaning a DNA sequence containing recognition sequences of at least one restriction enzyme, preferably of two or more restriction enzymes.

In an especially preferred embodiment, a vector according to the invention additionally also comprises a sequence for transcription termination, for example that of the octopine synthase gene, downstream of the promoter or the polylinker.

Likewise, the present invention relates to vectors comprising expression cassettes according to the invention. If appropriate, the vectors according to the invention comprise selection markers which are suitable for identifying, and, if appropriate, selecting, cells comprising the vectors according to the invention.

In a preferred embodiment, the vectors according to the invention are suitable for transforming plant cells, especially preferably for integrating foreign DNA (for example transgenes) into the plant genome. An example of such vectors are binary vectors, some of which are commercially available.

The present invention furthermore relates to host cells which are genetically modified with a nucleic acid molecule according to the invention (i.e. promoter according to the invention), an expression cassette according to the invention or a vector according to the invention, in particular plant cells or microbial cells, for example of the genus *Agrobacterium*.

In this context, "genetically modified" means that the host cell comprises a promoter according to the invention, an expression cassette according to the invention or a vector according to the invention, preferably stably integrated into the genome of the host cell, and that the promoter, or the expression cassette, has been introduced as foreign DNA into the host cell or a precursor of this cell. This means that the host cells according to the invention can either be themselves the immediate product of a transformation event or else be cells derived therefrom and which comprise a promoter according to the invention or an expression cassette according to the invention. Suitable host cells are prokaryotic, in particular bacterial, cells or else eukaryotic cells. Eukaryotic cells can be, for example, fungal cells, in particular those of the genus *Saccharomyces*.

In a further embodiment, the invention relates to the use of vectors according to the invention, expression cassettes according to the invention or host cells according to the invention, in particular host cells of the genus *Agrobacterium*, for transforming plants, plant cells, plant tissues or plant parts.

In an especially preferred embodiment, the host cells according to the invention are plant cells, termed "transgenic plant cells" hereinbelow.

Furthermore, the present invention also relates to plants comprising plant cells according to the invention. In principle, these plants may belong to any plant species, plant genus, plant family, plant order or plant class which is commercially utilizable. They may be monocots or else dicots. The plants according to the invention are preferably useful plants, i.e. plants which are of agricultural, silvicultural and/or horticultural interest. Preferred in this context are agricultural useful plants, in particular cereal species such as, for example, wheat, oats, barley, rye, maize, rice or fodder and forage grasses (such as, for example alfalfa, white clover or red clover).

In a further embodiment, the present invention also relates to methods for generating transgenic plant cells and plants, which comprises transforming plant cells, plant tissues, plant parts or protoplasts with a nucleic acid molecule according to the invention, a vector according to the invention, an expression cassette according to the invention or with a host cell according to the invention, preferably a microorganism, growing the transformed cells, tissues, plant parts or protoplasts in a growth medium, and, when transgenic plants are generated, regenerating plants from these.

In a further embodiment, the invention relates to the use of one or more of the nucleic acid molecules, vectors, expression cassettes or, if appropriate, host cells according to the invention for generating transgenic host cells, in particular transgenic plant cells and plants.

In a further embodiment, the invention relates to a method for the caryopsis-specific gene expression in plants, wherein one or more of the nucleic acid molecules according to the invention is integrated stably into the genome of a plant cell, either directly or by means of one or more of the vectors, expression cassettes or host cells according to the invention, and a plant is regenerated from said plant cell.

In a further embodiment, the invention relates to a method for the caryopsis-specific gene suppression in plants, wherein one or more of the nucleic acid molecules according to the invention is integrated stably into the genome of a plant cell, either directly or by means of one or more of the vectors, expression cassettes or host cells according to the invention, and a plant is regenerated from said plant cell, preferably by means of cosuppression.

The plants according to the invention can be generated by methods known to the skilled worker, for example by transforming plant cells or tissue and regenerating intact plants from the transformed cells or the tissue.

A multiplicity of techniques is available for introducing DNA into a plant host cell. These techniques comprise the transformation of plant cells with T-DNA using *Agrobacterium tumefaciens* or *Agrobacterium rhizogenes* as transformation agent, the fusion of protoplasts, the injection, the electroporation of DNA, the introduction of the DNA by means of the biolistic approach, and other possibilities.

When DNA is injected and electroporated into plant cells, no specific requirements as such are made to the plasmids used. Simple plasmids such as, for example, pUC derivatives can be used. However, if intact plants are to be regenerated from cells transformed thus, for example the presence of a selectable marker gene is necessary.

Depending on the method by which desired genes are introduced into the plant cell, further DNA sequences may be required. If, for example, the Ti or Ri plasmid are used for transforming the plant cell, at least the right border, but frequently the right and left border, of the Ti and Ri plasmid T-DNA must be linked to the genes to be introduced as flanking region.

If agrobacteria are used for the transformation, the DNA to be introduced must be cloned into specific plasmids, viz. either into an intermediary vector or into a binary vector. The intermediary vectors can be integrated into the Ti or Ri plasmid of the agrobacteria by homologous recombination owing to sequences which are homologous to sequences in the T-DNA. This Ti or Ri plasmid additionally contains the vir region, which is necessary for transferring the T-DNA. Intermediary vectors are not capable of replication in agrobacteria. The intermediary vector can be transferred to *Agrobacterium tumefaciens* by means of a helper plasmid (conjugation). Binary vectors are capable of replicating both in *E.coli* and in agrobacteria. They contain a selection marker gene and a linker or polylinker, which are framed by the right and left T-DNA border region. They can be transformed directly into the agrobacteria (Holsters et al. Mol. Gen. Genet. 163 (1978), 181–187). The agrobacterium acting as the host cell should contain a plasmid carrying a vir region. The vir region is necessary for transferring the T-DNA into the plant cell. Additional T-DNA may be present. The agrobacterium transformed thus is used to transform plant cells.

The use of T-DNA for transforming plant cells has been studied intensively and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

To transfer the DNA into the plant cell, plant explants can expediently be cocultured together with *Agrobacterium tumefaciens* or *Agrobacterium rhizogenes*. Then, intact plants can be regenerated from the infected plant material (for example leaf sections, stem segments, roots, but also protoplasts, or plant cells grown in suspension culture) in a suitable medium which may contain antibiotics or biocides for selecting transformed cells. The plants thus obtained can then be examined for the presence of the DNA introduced. Other possibilities of introducing foreign DNA using the biolistic method or by protoplast transformation have been described (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basle-Cambridge).

Monocots have already been routinely transformed by means of the biolistic approach and by means of agrobacteria (Komari et al., (1998); Advances in cereal gene transfer; Current Opinion in Plant Biotechnology 1, p. 161 et seq.; Bilang et al. (1999), Transformation of Cereals, Genetic Engineering, 12, pp. 113–148 Ed.: J K Setlow, Kluwer Academic/Plenum Publisher, New York). Other suitable methods are the electrically or chemically induced DNA uptake into protoplasts, the electroporation of partially permeabilized cells, the macroinjection of DNA into inflorescences, the microinjection of DNA into microspores and proembryos, the DNA uptake by germinating pollen, and the DNA uptake into embryos by swelling (review: Potrykus, Physiol. Plant (1990), 269–273).

In addition, protoplast transformation, the electroporation of partially permeabilized cells, or the introduction of DNA by means of glass fibers, constitute alternative methods with which the skilled worker is familiar.

The successful transformation of other cereal species has also been described, for example in the case of barley (Wan and Lemaux, see above; Ritala et al., see above; Kerns et al., Nature 296 (1982), 72–74) and wheat (Becker et al., Plant J. (1994) 5 (2): 229–307; Nehra et al., Plant J. 5 (1994), 285–297).

For rice, different transformation methods have been described, such as, for example, the agrobacterium-mediated transformation (Hiei et al., Plant J. 6 (1994), 271–282; Hiei et al., Plant Mol. Biol. 35 (1997), 205–218; Park et al., J. Plant Biol. 38 (1995), 365–371), protoplast transformation (Datta, In "Gene transfer to plants", Potrykus, Spangenberg (Eds.), Springer-Verlag, Berlin, Heidelberg, 1995, 66–75; Datta et al., Plant Mol. Biol. 20 (1992), 619–629; Sadasivam et al., Plant Cell Rep. 13 (1994), 394–396), the biolistic approach for plant transformation (Li et al., Plant Cell Rep. 12 (1993), 250–255; Cao et al., Plant Cell Rep. 11 (1992), 586–591; Christou, Plant Mol. Biol. (1997), 197–203) and electroporation (Xu et al., In "Gene transfer to plants", Potrykus, Spangenberg (Eds.), Springer-Verlag, Berlin, Heidelberg, 1995, 201–208).

The present invention furthermore also relates to the propagation material and harvested material of the plants according to the invention, which comprises plant cells according to the invention. In this context, the term "propagation material" extends to all those constituents of the plant which are suitable for generating progeny via the vegetative or generative route. Examples which are suitable for vegetative propagation are cuttings, callus cultures, rhizomes, root stocks or tubers. Other propagation material encompasses, for example, fruits, seeds, seedlings, protoplasts, cell cultures and the like. The propagation material is preferably tubers or seeds.

The present invention furthermore relates to the use of promoters according to the invention, or to the promoters identified by means of the method according to the invention, for the caryopsis-specific expression of transgenes in plant cells or plants.

Moreover, the present invention relates to the use of the promoters according to the invention, or of the promoters identified by means of the method according to the invention, for the caryopsis-specific cosuppression of genes or transgenes in plant cells or plants.

In this context, the term "transgene" is to be understood as meaning a DNA sequence which has been introduced artificially into a plant and which contains one or more of the nucleic acid molecules according to the invention.

These and other embodiments are disclosed to the skilled worker by the description and the examples of the present invention. Further literature on the abovementioned methods, means and applications required for the purposes of the present invention is known to the skilled worker from the prior art. The methods of choice which are suitable for this purpose are, inter alia, public databases (for example "Medline"), some of which are available via the Internet, for example under the web site http://www.ncbi.nlm.nih.gov/PubMed/medline.html. Other databases and addresses are known to the skilled worker and can be found on the Internet, for example on the web site http://www.lycos.com. An overview over sources and informations on patents or patent applications in biotechnology can be found in Berks, TIBTECH 12 (1994), 352–364.

To describe the invention more specifically, one of the promoters is represented by SEQ ID No. 1, consisting of 3 809 bases of the genomic sequence of the isolated gbss I subclone p11/1 such as deposited by DSM 13398. Present therein are 3 163 bases of the 5'-flanking regions and 646 bases of the coding region of GBSS I. Comparisons of the genomic sequence shown in SEQ ID No. 1 with the isolated cDNA clone of GBSS I (Block (1997) PhD thesis, University of Hamburg) show, in the 5'-untranslated region, a homology with the cDNA clone of approximately 75% at positions 2 333 to 2 436 and a homology 100% with the cDNA clone at positions 3 216 to 3 262. The 5'-untranslated region of the gene is interrupted by a leader intron approximately 670 bases in length (positions 2 436–3 101 in SEQ ID No. 1).

The DNA-region flanking the start codon 5' (promoter and 5'-untranslated region with leader intron; SEQ ID. No. 1 positions 1–3 139) was studied for known cis-regulatory DNA elements of plants. Endosperm- or seed-specific DNA elements were identified at the following positions in the GBSS I promoter (=SEQ ID No. 1):

```
-300 bp elements (TGTAAAG)   position 906  (-) TGHAAARK

RY repeat (CATGCATG)         position 2138 (+) CATGCATG
                             position 929  (+) CATGCAT
                             position 989  (-) CATGCAT
                             position 270  (-) CATGCAT
                             position 2139 (-) CATGCAT ACGT motif                   position 1346 (+) GTACGTG
                             position 1401 (+) GTACGTG
                             position 1836 (+) GTACGTG Amylase box                  position 2488 (-) TATCCAT
```

-continued

```
E boxes (CANNTG)          position 451  (+) CANNTG
                          position 942  (+) CANNTG
                          position 967  (+) CANNTG
                          position 987  (+) CANNTG
                          position 997  (+) CANNTG
                          position 1038 (+) CANNTG
                          position 1140 (+) CANNTG
                          position 1363 (+) CACGTG (G box)
                          position 1571 (+) CANNTG
                          position 1988 (+) CANNTG
                          position 2014 (+) CANNTG
                          position 2035 (+) CANNTG
                          position 2554 (+) CANNTG
                          position 3032 (+) CANNTG
                          position 1050 (-) CACGTG (G box)
                          position 1695 (-) CACGTG (G box)
                          position 2949 (-) CACGTG (G box)

Napin motif (TACACAT)     position 308  (+) TACACAT
                          position 940  (+) TACACAT
                          position 264  (-) TACACAT SEF4 motif                position 330  (+) RTTTTTR
                          position 2868 (+) RTTTTTR
                          position 241  (+) RTTTTTR
                          position 639  (+) RTTTTTR
                          position 2878 (+) RTTTTTR
                          position 721  (-) RTTTTTR
                          position 2657 (-) RTTTTTR
                          position 3038 (-) RTTTTTR
```

DNA elements for pollen-specific gene expression were found at the following positions:

```
Pollen 1                  position 609  (+) AGAAA
(LAT52; L. esculentum)    position 702  (+) AGAAA
                          position 1053 (+) AGAAA
                          position 1057 (+) AGAAA
                          position 1449 (+) AGAAA
                          position 3046 (+) AGAAA
                          position 27   (-) AGAAA
                          position 104  (-) AGAAA
                          position 141  (-) AGAAA
                          position 254  (-) AGAAA
                          position 409  (-) AGAAA
                          position 520  (-) AGAAA
                          position 559  (-) AGAAA
```

-continued
```
                          position 563  (-) AGAAA
                          position 656  (-) AGAAA
                          position 771  (-) AGAAA
                          position 822  (-) AGAAA
                          position 2707 (-) AGAAA
                          position 2812 (-) AGAAA
                          position 2819 (-) AGAAA
                          position 2923 (-) AGAAA Q element (ZM13)          position 2842 (+) AGGTCA
                          position 2847 (+) AGGTCA
```

DNA elements involved in a sugar-regulated gene expression were found at the following positions:

```
TATCCAY motif             position 2488 (-) TATCCAY

CGACG element (AMY3, O. sativa)   position 1761 (+) CGACG
                                  position 1289 (-) CGACG
                                  position 1488 (-) CGACG
                                  position 1748 (-) CGACG
                                  position 932  (-) CGACG
```

Root-specific DNA elements were found at the following positions:

```
Root motif (Triticum aestivum POX1)  position 63  (+) ATATT
                                     position 278 (+) ATATT
                                     position 501 (+) ATATT
                                     position 753 (+) ATATT
                                     position 890 (+) ATATT
                                     position 277 (-) ATATT
                                     position 304 (-) ATATT
                                     position 870 (-) ATATT
```

DNA elements involved in a hormonally regulated gene expression by ABA were found at the following positions:

```
ABRE motif (Oryza sativa em)        position 1347 (+) TACGTGTC
                                    position 1067 (-) TACGTGTC ABRE motif (Triticum aestivum L. Em) position 1930 (+) ACGTSSSC DPBF Core (CDC3)                    position 941  (+) ACACNNG
                                    position 951  (+) ACACNNG
                                    position 966  (+) ACACNNG
                                    position 996  (+) ACACNNG
                                    position 1010 (+) ACACNNG
                                    position 1025 (+) ACACNNG
                                    position 1107 (+) ACACNNG
                                    position 1570 (+) ACACNNG
                                    position 1603 (+) ACACNNG
                                    position 2077 (+) ACACNNG
                                    position 296  (-) ACACNNG
```

DNA elements involved in a hormonally regulated gene expression by auxin or ethylene were found at the following positions:

Auxin response factor (ARF A.thaliana) position 2984 (−) TGTCTC

```
Auxin response factor   position 2984 (-) TGTCTC
(ARF A. thaliana)

NtBBF1 motif (roIB)     position 614 (+) ACTTTA
                        position 793 (+) ACTTTA Ethylene RE             position 3022 (+) AWTTCAAA
(L.esculentum4)         position 3028 (+) AWTTCAAA
```

DNA elements which represent a light- or temperature-regulated gene expression were found at the following positions in the GBSS I promoter:

```
I box                   position 713  (-) GATAA
                        position 796  (-) GATAA
LowTemperature RE       position 1019 (-) ACCGACA
(H. vulgare)
LowTemperature RE       position 1020 (+) COGAC
(A.thaliana)            position 1324 (+) CCGAC
                        position 1749 (-) CCGAC
                        position 2523 (-) CCGAC
```

AT-rich regions, as they are known from various other promoters as enhancer elements (J. E. Sandhu, 1998, Plant Mol. Biol. 37: 885–96) are found in the promoter represented by SEQ ID No. 1 at various positions: positions 1–958, 1024–1213, 1912–1960 and 2527–3127. A basal DNA element which is essential for the initiation of transcription (TATA box) was found at position 2378. According to Nikolov (D. B. Nikolov, 1997, PNAS 94: 15–22), the point where transcription is initiated lies 25 bp downstream of the TATA box.

Besides other DNA motifs (CAAT box, GT1 box, MART boxes, DOF boxes, Myb and Myc boxes), the promoter stated under SED ID No. 1 contains further, as yet unknown sequence motifs. One DNA sequence motifs. One DNA motif (CCACACACTACAA) (SEQ ID NO: 11) at position 2283 shows homologies with DNA sequence segments of the barley gbss I promoter and a DNA region in the wheat puroindolin promoter (Digeon et al. (1999) Plant Mol Biol. 39: 1101–1112; Acc. No. AJ000548), which regulates expression of the GUS reporter gene in endosperm, aleuron cells and in the pericarp in rice. Repeats of sequence $(CA)_n$ are located at positions 948–956, 1 007–1 015 and 1 024–1 030. A repeating sequence motif (CTCACC) is located at positions 1 259 and 1 267. Two direct sequence repeats (ACGTACGT) are located at positions 1 344 and 1 349.

Further sequence repeats (GAGAGC) are located at position 1 558, position 1 614 (CGCGTG) and 1 644 (CCCACCGG). A motif of the sequence $(AAAC)_4$ is located at position 1 887. A repeating motif of sequence $(GAA)_n$ is located at positions 2 321 and 2 379 to 2 423. Sequence regions which exhibit homologies with the barley GBSS I promoter region (Genlibrary Acc. No. X07931) are located at positions 1 383–1 406 (sequence identity 95%), 2 136–2 179 (sequence identity 93%) and 2 229–2 284 (sequence identity 90%).

Deposition of Microorganism:

The nucleic acid molecule according to the invention as shown in SEQ ID No. 1 was disclosed at the Deutsche Sammlung für Mikroorganismen und Zelikulturen (DSMZ) in Brunswick, Germany, in compliance with the provisions of the Budapest Treaty on Mar. 17, 2000 (03.17.2000) by depositing plasmid DNA: plasmid p11/1 comprising SEQ ID No. 1, deposition number DSM 13398.

Cloning Methods

The vectors pBluescrip™ II, SK(+/−) and KS(+/−) phagemid vectors (Stratagene GmbH, Heidelberg, Germany) and Lambda Fix® II/XhoI cloning vector (Stratagene GmbH, Heidelberg, Germany) were used for cloning into E.coli bacterial strains.

Bacterial Strains

The E.coli strains DH5α (Life Technologies, Karlsruhe, Germany) and Epicurian Coli SURE® (Stratagene GmbH, Heidelberg, Germany) were used for the Bluescript vectors. The Epicurian Coli strain XL1-Blue MRA (Stratagene) was used for the bacteriophage vectors.

As regards basic techniques in molecular biology, reference is made to Sambrook et al. 1989: Sambrook et al. (1989), Molecular Cloning; A Laboratory Manual, Second Edition; Cold Spring Harbour Laboratory Press).

USE EXAMPLES

The examples which follow illustrate the invention, but do not limit it in any way whatsoever.

1. Generation of the Genomic Wheat Library

To generate the genomic wheat library, total DNA was isolated from etiolated seedlings of Triticum aestivum L. cv. "Florida". To grow sterile etiolated seedlings, mature caryopses were incubated for 20 min in 1% NaOCl, 0.1% (v/v) Mucasol® (Merz & Co., Frankfurt, Germany) and subsequently washed 3× with ddH$_2$O. The caryopses were plated onto sterile MS medium (Murashige & Skoog (1962), Physiol. Plant. 15: 473–479), to which 0.3% (w/v) of GELRITE® (Carl Roth GmbH & Co., Karlsruhe, Germany) had been added for solidification. Growth took place in the dark at 26° C. Fourteen days after plating, the seedlings were cut off and frozen in liquid nitrogen.

The genomic DNA was digested partially with the restriction enzymes BamH I or Sau3A I (Life Technologies, Karlsruhe, Germany). To this end, 3 aliquots in each case comprising 100 μg genomic DNA and 150 μl of the restriction buffers were restricted for 1 h at 37° C. in a total volume of 1.5 ml with 12.5 units, 6.25 units or 3.125 units of the restriction enzyme BamH I or with 1.56 units, 0.78 units or 0.39 units of Sau3A I. Aliquots of the partially restricted DNA were then analyzed by gel electrophoresis for the degree of restriction. The restriction enzymes were removed from the reactions by extracting once with phenol/chloroform/isoamyl alcohol (25:24:1, v/v) and chloroform/isoamyl alcohol (24:1, v/v). Finally, sucrose was added to each reaction to a final concentration of 10% (w/v).

Size fractionation of the partially restricted DNA was effected in continuous 10–40% sucrose gradients (w/v) (Sambrook et al. (1989)). Prior to application to in each case a 15 ml sucrose gradient, the individual aliquots of the partially restricted DNAs were warmed for 10 min at 68° C. and then cooled to 20° C. The gradient was centrifuged for 24 h at 20° C. and 22 000 rpm (Beckmann, Rotor SW 40). After centrifugation, the bottoms of the centrifuge tubes were pierced, and 500 μl aliquots were collected. 30 μl from the individual fractions were separated in a 0.5% agarose gel, and the size distribution of the DNA in the individual fractions was determined. Fractions containing genomic DNA of approx. 4.0 kb and above were combined. The sucrose from the samples was removed by dialysis against Tris/EDTA buffer (10 mM/1 mM). The samples were subsequently concentrated with 2-butanol and the DNA was precipitated from the samples at room temperature (RT) with 2 volumes of EtOH (99.8%)/2 M ammonium acetate (final concentration).

To fill up the 3' end of the partially restricted DNA, 20 μg of the DNA restricted with BamH I or Sau3A I were incubated in a final volume of 60 μl with 1 mM dATP, 1 mM dGTP (Roche, Mannheim), 6 μl 10× Pfu reaction buffer and 10 units native Pfu-DNA polymerase (DNA polymerase with proof-reading activity; Stratagene GmbH, Heidelberg, Germany). The reaction was carried out for 1 h 30 min at 72° C. The DNA was subsequently extracted with phenol/chloroform/isoamyl alcohol and with chloroform/isoamyl alcohol and subsequently precipitated with 1/10 volume 3M NaAc and 2.5 volumes absolute EtOH.

1.1. Ligation into Lambda Fix® II/Xho I Partial Fill-in Vectors (Stratagene GmbH, Heidelberg, Germany)

The genomic DNA which have been restricted with BamH I or Sau3A I was ligated into the Lambda Fix® II/Xho I cloning vector following the manufacturer's instructions (Stratagene GmbH, Heidelberg, Germany). The ligation reaction contained: 1 μl of the Lambda Fix® II vector, 0.4 μg of genomic DNA restricted with BamH I or Sau3A I, 0.5 μl 10× ligation buffer, 2 Weiss units T4 DNA ligase (MBI Fermentas GmbH, St. Leon-Rot, Germany); Weiss et al. (1968) J. Biol. Chem., 243: 4543–4555) in a final volume of 5 μl.

1.2. In vitro Packaging of the Ligation Products

To package the Lambda phages, the in vitro packaging kit "Gigapack® II Gold" by Stratagene (Stratagene GmbH, Heidelberg, Germany) was used, following the manufacturer's instructions. 1 μl of each of the ligation reactions was added to the packaging reactions; the rest was as described in the manufacturer's instructions.

1.3. Growing Bacteria for Phage Amplification

The *E.coli* bacterial strain XL1-Blue MRA (P2) was used for phage amplification. The bacteria were grown in LB medium supplemented with 10 mM $MgSO_4$, 0.2% (w/v) maltose, to an $OD_{600}$=0.5 at 37° C., 180 rpm. The bacteria was subsequently pelleted for 10 min at 4° C. at 2 000 rpm and the supernatant was discarded. The bacterial pellet was resuspended in 10 mM $MgSO_4$ and the bacterial density was adjusted to $OD_{600}$=0.5.

For phage amplification, from the packaging reactions 1 μl from the original reactions or 1:10 dilution of the original reactions were mixed with 200 μl of bacterial suspension ($OD_{600}$=0.5) and incubated for 15 min at 37° C. The individual reactions were subsequently mixed with 3 ml of TOP agarose (48° C.) and plated onto solid NZY medium following the manufacturer's instructions (see above Lambda Fix® II/Xho I Partial Fill-In vectors, Stratagene). The plates were incubated for approximately 16 h at 33° C.

The phage titer of the genomic Sau3A I or BamH I libraries were determined by counting the phage plaques. For the primary Sau3a I or BamH I libraries, phage titers of $2.2 \times 10^7$ pfu/ml and $1.4 \times 10^7$ pfu/ml, respectively, were determined. To determine the average insert sizes, 10 individual phage clones from each library were amplified, the phage DNA was isolated (Sambrook et al. 1989), and the insert sizes were determined following restriction digestion and separation by gel electrophoresis. The average insert size is approx. 15.0 kb for the BamH I library and 15.6 kb for the Sau3A I library.

1.4. Amplification of the Genomic Libraries

To generate representative amplified genomic libraries, approx. 4.5 million pfu from each library were plated. Amplification was performed following the manufacturer's instructions (Stratagene). The phage titers of the amplified libraries were $6.3 \times 10^9$ pfu/ml (BamHI library) and $2.0 \times 10^9$ pfu/ml (Sau3A I library).

2. Screening of the Genomic Libraries

Phage clones whose genomic inserts carry sequences of the gbss I genes were identified and isolated via plaque hybridization. To screen the genomic libraries, approx. 500 000 phages from each library were plated out. The phages were plated out and the plates were lifted following standard protocols (Sambrook et al., 1989; Stratagene Lambda Fix® II Manual). DNA fragments of cDNA clones of GBSS I (Block, M. (1997) "Isolierung, Charakterisierung und Expressionsanalysen von Stärkesynthase-Gene aus Weizen [Isolation, characterization and expression analyses of wheat starch synthase genes] (*Triticum aestivum* L.)", PhD thesis, University of Hamburg) were employed as gene-specific probes.

A 283 bp DNA fragment of the gbss I cDNA clone was labeled in a specific PCR reaction with incorporation of DIG-labeled dUTPs (Roche Diagnostics GmbH, Mannheim, Germany). The PCR reaction was carried out with primers positioned within the first exon of the gbss I cDNA clone (positions 146–429).

W1: 5'-ATGGCGGCTCTGGTCACGTC-3' (SEQ ID No. 9)
W2: 5'-AGGCCGCCAGTCTTGCTCCA-3' (SEQ ID No. 10)

The PCR reaction was composed as follows:
10 μl PCR buffer (10× conc.; Life Technologies)
3 μl $MgCl_2$ (50 mM; Life Technologies)
3 μl DIG dUTPs (Roche Diagnostics GmbH, Mannheim)
3 μl dNTP mix (5 mM of each)
6 μl primer W1 (10 pmol)
6 μl primer W2 (10 pmol)
10 ng template (cDNA clone of gbss I)
1 μl Taq polymerase (5 U/μl; Life Technologies)
$ddH_2O$ to 100 μl The PCR conditions were as follows:
I. 94° C., 5 min
II. 94° C., 30 sec
III. 62° C., 30 sec
IV. 72° C., 60 sec (IV.→II.29 loops)
V. 72° C., 5 min The filters were prehybridized in 5×SSC, 3% blocking reagent (Boehringer Mannheim), 0.2% sodium dodecyl sulfate (SDS), 0.1% N-laurylsarcosin and 30 µg/ml herring sperm DNA in a water bath at 65° C. Hybridization with the DIG-labeled DNA probes (6 ng/ml hybridization solution) was carried out overnight at 65° C. in the above-described standard hybridization buffer. All further steps of the CSPD® chemoluminescence reaction were performed following the manufacturer's instructions (Roche Diagnostics GmbH, Mannheim, Germany).

Positive plaques were picked out and singled out over two individual amplification and plaque filter hybridization passages. The DNA of the isolated positive phages were purified with the Qiagen® Lambda Kit (Qiagen GmbH, Hilden, Germany), cleaved with various restriction enzymes and, following agarose gel electrophoresis, analyzed in Southern hybridizations with the probes which have already been described.

3. Subcloning of the λ-Phage Clones into Bacterial Vectors (pBluescrip™ II )

The genomic inserts of the positive phage clones were cleaved with various restriction enzymes. The resulting subfragments were cloned into bacterial vectors (pBluescript™ II SK(+/-) and KS(+/-) phagemid vectors; Stratagene GmbH, Heidelberg, Germany).

gbss I specific clones with 5'-upstream regulatory elements were isolated via Southern hybridizations.

4. Sequence Analyses

SeqLab GmbH (Göttingen) was commissioned to sequence the genomic clones of the gbss I and its 5'-upstream regulatory elements.

5. Cloning Promoter Test Vectors

The functionality of the 5'-flanking DNA regions stated in SEQ ID No. 1 were verified in transient and stable expression analyses. The reporter gene used was the β-glucuronidase (GUS) gene (Jefferson (1987) Plant Molecular Biology Reporter Vol.5 (4): 387–405). Promoter test vectors were cloned in which the coding region of the gus gene (uidA) is under the control of the 5'-flanking DNA region stated in SEQ ID No. 1 (positions 1–3 139). Cloning was performed as a transcriptional fusion. First, the uidA gene together with the nos terminator was excized from vector pCal-GUS (uidA gene under the control of the CaMV 35S promoter; Chris Warren, Stanford University, unpublished) via a partial digest and cloned behind the multiple cloning site of pBluescript (Stratagene). The promoter-free vector thus generated (uidA-nos) was used for the further cloning steps.

The 5'-untranslated leader sequence of an mRNA may also affect the tissue specific expression of a gene (Rouster et al. (1998) Plant J. 15 (3): 435–40). The cloned promoter test vectors therefore contain this region of the GBSS I gene. In the cloning strategy chosen, the β-glucuronidase start codon is at the position of the GBSS I start codons.

5.1. Cloning the Gbss I Promoter Test Vectors

The starting construct of the gbss I promoter test vector carries approximately 7.5 kb of the 5'-flanking DNA region of gbss I. Cloning into the promoter-free uidA-nos vector was performed via restriction digest of plasmids p11/1 (gbss I) and puidA-nos with the enzyme combinations Nco I/Xba I, NcoI/Sac I and for a partial digest with Nco I/Sal I. The 7.5 kb 5'-flanking region was subsequently truncated by different restrictions, leading to removal of DNA regions in which some of the above-described DNA elements are positioned.

The gbss I promoter test vector was deleted in the 5'-flanking region by restrictions with the restriction enzymes stated hereinbelow. In this manner, the following deletion constructs of the gbss I promoter were cloned:

−4.0 gbss I/gus (Sac I restriction approx. 4 kb upstream of the gbss I start codon; contains nucleotides 1–3 139 of SEQ ID No. 1);

−1.9 gbss I/gus (XbaI restriction at position 1 240; containing nucleotides 1 241–3 139 of SEQ ID No. 1);

−1.6 gbss I/gus (SmaI restriction at position 1 514; containing nucleotides 1 515–3 139 of SEQ ID No. 1);

−1.3 gbss I/gus (Kpn I restriction at position 1 826; containing nucleotides 1 827–3 139 of SEQ ID No. 1);

−1.0 gbss I/gus (BamH I restriction at position 2 176; containing nucleotides 2 177–3 139 of SEQ ID No. 1) and −0.4 gbss I/gus (Bgl II restriction at position 2 727; containing nucleotides 2 692–3 139 of SEQ ID No. 1).

6. Transient Expression Analyses of the Promoter Test Vectors

The functionality of the promoter constructs isolated was verified in transient expression analyses. The tests were carried out with the gbss I promoter test vectors and their deletion constructs of Example 5.

The transient expression analyses were carried out following the biolistic transformation of various tissues (caryopses, embryos, leaves, roots) of wheat. Embryos, leaves and roots were transformed as described by Becker et al. (Plant J. (1994)5 (2): 229–307), while the biolistic transformation of the endosperm of caryopses was carried out following a modified method of Mena et al. (Plant J. (1998) 16(1), 53–42). The reporter gene activity was detected by histochemically detecting GUS activity (Jefferson (1987) Plant Molecular Biology Reporter Vol.5 (4): 387–405). The experiments on 10–30 day old (dap) wheat caryopses which had been cut horizontally and vertically demonstrated that the promoter leads to expression of the reporter gene in endosperm. In the transient tests, the activity of the uidA reporter gene under the control of the gbss I promoter was relatively highly pronounced.

6.1. The Following Deletion Constructs of the GBSS I Promoter Proved to be Functional in Transient Expression Analyses:

−7.5 gbss I/gus (contains approx. 7.5 kb upstream of the gbss I start codon; including nucleotides 1–3 139 SEQ ID No. 1)

−4.0 gbss I/gus, containing nucleotides 1–3 139 of SEQ ID No. 1)

−1.9 gbss I/gus (Xba I restriction at position 1 240)

−1.6 gbss I/gus (Sma I restriction at position 1 514)

−1.3 gbss I/gus (Kpn I restriction at position 1 826)

−1.0 gbss I/gus (Bam H I restriction at position 2 176)

Following a deletion at position 2 691 of SEQ ID No. 1 (−0.4 gbss I/gus), GUS activity of the reporter gene was no longer detectable.

7. Stable Transformation of Wheat with the Promoter Test Vectors

The promoter test vectors and deletion constructs described in Example 5 were used to generate stably transformed wheat plants:

−4.0 gbss I/gus (see above)
−1.9 gbss I/gus (Xba I restriction at position 1 240; SEQ ID No. 1)
−1.0 gbss I/gus (BamH I restriction at position 2 176; SEQ ID No. 1)

The transgenic plants were generated following the method of Becker et al. (Plant J. (1994) 5 (2): 229–307). The selection markers used were plasmids p35S-PAT (Aventis CropScience GmbH, Frankfurt) and pAct1Dneo (Müller (1992) PhD, University of Hamburg), which carry glufosinate resistance and neomycin resistance, respectively.

8. Analysis of the Gus Reporter Gene Expression in Stably Transformed Wheat Plants The functional analysis of the gbss I promoters was carried out following regeneration of the transgenic plants and the verification of stable and complete integration of the test constructs into the wheat genome via Southern analyses.

The reporter gene activity in the transgenic plants regenerated was studied via a histochemical GUS detection. Various tissues of the transgenic plants (leaves, roots, stems, endosperm, embryo, pollen) were analyzed. The caryopses of the plants stably transformed with the gbss I test vectors show pronounced GUS staining in the central starch endosperm. The GUS activity was detected even in very young caryopses in the developing endosperm. Moreover, an activity of the gus reporter gene in the pericarp is detectable very soon after pollination, a phenomenon no longer found in older caryopses. In contrast, no GUS activity was detected in the embryo, the aleuron and the region surrounding the embryo; nor was any reporter gene activity detected in the assimilating tissue of the leaves and in the stems and roots. GUS activity was also detected in transgenic pollen. Quantitative analyses of the expression of the reporter gene were performed via fluorimetric GUS detections and in Northern blot analyses.

TABLE 1

Expression pattern of the gbss I promoter construct (cf. Ex. 5–7)

| Tissue | −4.0 GUS | −1.9 GUS | −1.0 GUS |
|---|---|---|---|
| Endosperm | | | |
| young | ++ | ++ | + |
| old | +++ | +++ | − |
| Pericarp | | | |
| young | + | + | + |
| old | − | − | − |
| Chlorophyll layer | − | − | − |
| Embryo | − | − | − |
| Scutellum | − | + | + |
| Pollen | +++ | +++ | + |
| Leaf | − | − | − |

It emerged that the degree of β-glucuronidase activity, or of reporter gene expression, decreases with the decreasing length of the promoter fragment integrated into the promoter test vector. An explanation for this effect is the presence of AT-rich regions, which gradually disappear as the promoter region is truncated. They are found in positions 1–958, 1 024–1 213 and 1 912–1 960 in the region of the construct −4.0 gus, the first two being deleted upon truncation to give the construct −1.9 gus. Further truncation to give the construct −1.0 gus also results in the deletion of the AT-rich region 1 912–1 960. What is surprising is that even the −1.0 gus construct mediates tissue-specific activity, since in this deletion only 38 bp are present of the region which 5'-flanks the TATA box and in which the cis-regulatory DNA elements are usually present.

Northern blot analyses showed the expression patterns of the different promoter GUS constructs. The uidA expression pattern during the caryopsis development of the plants which contain the construct −4.0 gus corresponded to that of the gbss 1 gene, both in the endosperm and in the pericarp. The −1.9 GUS construct and the −1.0 GUS construct also led to a uidA expression pattern in the pericarp which corresponded to that of the gbss 1 gene. As regards the expression of the uidA reporter gene under the control of these two promoter deletions in the endosperm, the activity maximum was shifted greatly toward a later point in time of caryopsis development; it was approximately 25 days after pollination or later.

What is claimed is:

1. An isolated nucleic acid molecule with the function of a caryopsis-specific promoter, which nucleic acid molecule:
   a) comprises the nucleic acid sequence defined by SEQ ID NO: 1 or deposited by DSM 13398 (plasmid p 11/1);
   b) comprises a functional portion of SEQ ID NO: 1;
   c) comprises a sequence which hybridizes with SEQ ID NO: 1, or the complement thereof, under hybridization conditions comprising a hybridization temperature of 65–68° C., a hybridization buffer salt concentration of 2×SSC, a wash temperature o 65–68° C., and a wash buffer salt concentration 0.2×SSC; and/or
   d) comprises a sequence which has approximately 95–99% identity with SEQ ID NO: 1.

2. An expression cassette comprising the isolated nucleic acid molecule as claimed in claim 1.

3. A vector comprising the isolated nucleic acid molecule as claimed in claim 1.

4. The vector as claimed in claim 3 which is suitable for transforming plant cells.

5. A host cell comprising the isolated nucleic acid molecule as claimed in claim 1.

6. The host cell as claimed in claim 5, which is a pro- or eukaryotic cell.

7. The host cell as claimed in claim 5, which is a plant cell.

8. A plant comprising the plant cell as claimed in claim 7.

9. Propagation material or harvested material from the plant as claimed in claim 8.

10. A method of generating transgenic plant cells, comprising the steps of transforming plant cells, plant tissue, plant parts or protoplasts with the isolated nucleic acid molecule as claimed in claim 1, the vector as claimed in claim 3, the expression cassette as claimed in claim 2, or the host cell as claimed in claim 5, and growing the transformed plant cells, plant tissues, plant parts or protoplasts in a growth medium.

11. A method of generating transgenic plants, comprising the steps of transforming plant cells, plant tissue, plant parts or protoplasts with the isolated nucleic acid molecule as claimed in claim 1, the vector as claimed in claim 3, the expression cassette as claimed in claim 2, or the host cell as claimed in claim 5, growing the transformed plant cells, plant tissues, plant parts or protoplasts in a growth medium, and regenerating intact plants from these.

12. A method for caryopsis-specific expression of genes in genetically modified plants comprising transforming a plant cell, plant tissue, plant part or protoplast with the nucleic acid molecule as claimed in claim 1, wherein the nucleic acid molecule drives expression of genes under the control of the nucleic acid molecule in caryopses.

13. A method for the caryopsis-specific suppression of genes in genetically modified plants comprising transforming a plant cell, plant tissue, plant part or protoplast with the nucleic acid molecule as claimed in claim 1, wherein a nucleic acid molecule under the control of the caryopsis-specific promoter suppresses expression of endogenous genes.

14. A method for caryopsis-specific gene expression in plants, wherein a nucleic acid molecule as claimed in claim 1 is stably integrated into to the genome of a plant cell, and the plant is regenerated from said plant cell, whereby caryopsis-specific gene expression occurs in the plant.

15. A method for caryopsis-specific gene suppression in plants, wherein a nucleic acid molecule as claimed in claim 1 is stably integrated into the genome of a plant cell, and a plant is regenerated from said plant cell, whereby caryopsis-specific gene expression occurs in the plant.

* * * * *

SEQUENCE LISTING

<160> NUMBER OF SEQ ID NOS: 11

<210> SEQ ID NO 1
<211> LENGTH: 3785
<212> TYPE: DNA
<213> ORGANISM: Triticum aestivum

<400> SEQUENCE: 1

```
gtttggtttc gctgtttttc atttccttc ttcttaaggg gtaataccaa tgacagtaat      60
tcatattgtg taacagtgcg attcttgtgc caattatgta caatttcttt tgtaattgtt     120
tgtttcatgt tttatttcat tttctttact ttttagggta aaaccaatgc ccccaattca     180
ttctacctaa gaggaaattc agttttatac tagtttcagt tttattattg tttattaagt     240
```

-continued

```
gtttttagtt ggttttctca tttatgtgta tgcatgaata ttaggggtgt gtgtgcgtgt    300
gttaatatac acataagtat tatacaccca tttttgcagt cataaaatta tgcaatttca    360
gtacaaattg tgcgcaaact cttcttcatt ttttattttt tattttatt tcttctttaa    420 gggtaatacc aatgatacta atttatgcct catttggaaa tttcgttttg aaaattatgc    480
tagtacacac ttattcttgt atattatgga aaagcgcaat ttctgtgtaa gttttgtcat    540 tctgtattt ttttcatttt tctttcttct ggaagggtaa cactaatgcc actaattcat    600
tcttgcttag aaaactttag tattttgatt gtgttttagt ttttatttca ttttgtttct    660
tctttaaggg aaataccaat gccactaatc cattccatct tagaaaatct ctttatctta    720
caaaaactca acttttatat gcttattcgt gcatattata aaaagcacag tttctatcta    780
aattgcgtgc aaactttatc attatttgtc taaattaatt ttttctagaa tgatgatacc    840
aatgccacta attcattccg tgagcacgca atatgcggaa tgcctacgta tattagtggt    900
gtcgcatttt tcatctctca cgcatgggca tgcataccct acacatgcac acacgcat     960 acacaacaca tgagcactca cgcgagcaca tgcatacacc tgtgcgcaca cacgacac    1020 cgacacacac gcacagccac atgcgtgcac ttagaaagaa aaatagaca cgtatacatt   1080 ggactggcta gctatactac cgtgtaacac tagtacgttg gtgttgtacg acctattttc   1140
aggtgccaca gactagtatt ttcaggcgac tgggatatag ccacggccta ttgtttcgtg   1200
tcgtaggacg aaaacggtca tatatgtggc actggccttc tagagactct ccaagaggct   1260
caccacctca ccgtgagtga cagcccaccg tcgcgtaaac caccgcattt acgtttcccc   1320
gatccgacaa agccagggca cgcacgtacg tgtccatgtt ggcacgtgcg tgcgtccctc   1380
acgcgccggt ttggcagcac gtacgtgcta gctgttcata ccagagccgt acgtcaatca   1440
agcaaaagag aaaaagaagg ggcgaaaggt gatacgcccg gccgtgtcgt cgtgctgcag   1500
aggaagcaat cccgggccat gcagcgccat tgccacgccc cagcgaaaag cgaaggcgag   1560
agcgagagca cacatggccc ccagaactga aagcgaggga gcacacgaga aggcgcgtgc   1620
gcgtggacat cacagcagga acacccaccg gcagcccacc gggcgggcgc gggcaggaca   1680
agaagatgcg tgcacggcgc ggccggcaac ggaagggggc gccgccggcc gagcgcacgc   1740
aaaggcgcgt cggccagcca cgacgccgct ggaaagcgcg ccggcgaacc gagaatgtgc   1800
caggctgcca gccgctccgc ggtaccacta gtctcgtacg tgtgccactc cactccgctc   1860
cgctcggcac gcacgcacgc aggcagaaac aaacaaacaa acaaaaaagt gggtcattca   1920
ctccactcaa cgtcgccttt caggacgatg cttcggtgcc ttaagacacc taccttgtg    1980 tctatgacat gtgagcccaa cagatggctg gcccacatgt cagtgatcca aaggcaggtg   2040
cctttaaagc accgaagctg cgtcccgcct ttcattacac gggccatgca tgcgggtgcg   2100
tgccgtcccg tctaggcgtt cggtgtccgg ccgcgtgcat gcatgcacga ggagcggagc   2160
ggagcgggta ttggggatcc agccaccgga ggactgagcg agcgggcgag tacaaataac   2220
cccactcacc ggagccacgc accgttcgtt tccttgagtc ccgtcacttt cgcccgcccg   2280
ccccacacac tacaaccagg agcctcgatc tgccagtgaa gaagaagaag gacactcacg   2340
aatgcccggc cggcgactgt gagtacgctc ccgtccagga agaagaagaa gaagaagaag   2400
cagaagaaga agaagcagaa gaagagatca gaccaggtac gcacgaacgt atatagtcag   2460
gccggcccag ttcccggccg ccggacgatg gatagatcga tttagttcgg tctcaaatca   2520
aggtcggttg gtctagtagt agatagatcc atccaaatgc cgccatgttg ttagatccag   2580
agtctcttcc ttttttactta aagatcgcga gcgtaagttg aggatcttcc tatagattcg   2640
```

```
tagatttaaa atcatgtaaa aattaaaaaa aaagatttaa aatcatgtac tgctagctag    2700
gatggatttc tatgtgaacg atcttagatc tgcggaacag atccaatgga ttcatggccg    2760
gcctagggtt aattacgact agacagaggc agcataatgc gcgcataaac atttctgttt    2820
tctagccgag ttggatcaaa caggtcaggt cacgcaccaa ggctttgatt tttgtttgtt    2880
tttggcgtgg gcgttccact gcaccctaca gaacaaattc catttctcag ccagttccac    2940
cccgtgcacg cgatttaaca gcttattaat tactaccagt gcggagacag gttcatatat    3000
actctggtca tgttaatttg gatttcaaat tcaaatgtaa aatccagaaa acttgactgc    3060
aaattctggt ttacttcact actcactaac aatcagtgca gtcgtctctt gctgcaggta    3120
gccacaccct gcgcgcgcca tggcggctct ggtcacgtcc cagctcgcca cctccggcac    3180
cgtcctcagc gtcaccgaca gattccggcg tccaggtttt cagggcctga ggccccggaa    3240
cccggcggat gcggcgctcg gcatgaggac tgtcggagcg agcgccgccc caaagcaaag    3300
caggaaaccg caccgattcg accggcggtg cctctccatg gtggtgcgcg ccacgggcag    3360
cggcggcatg aacctcgtgt tcgtcggcgc cgagatggcg ccctggagca agactggcgg    3420
cctcggcgac gtcctcgggg gcctccccgc cgccatggcc gtaagcttgc gccactgcct    3480
tcttataaat gtttcttcct gcagccatgc ctgccgttac aacgggtgcc gtgtccgtgc    3540
aggccaacgg tcaccgggtc atggtcatct ccccgcgcta cgaccagtac aaggacgcct    3600
gggacaccag cgtcatctcc gaggtatata tccgccacat gaattatcac aattcacatg    3660
ctcctgcaca tttctgcaag actttactga ctggctggat ctcgcagatc aaggtcgttg    3720
acaggtacga gagggtgagg tacttccact gctacaagcg cggggtggac cgcgtgttcg    3780
tcgac                                                              3785

<210> SEQ ID NO 2
<211> LENGTH: 29
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 2
cacgcaaagg cgcgtcggcc agccacgac                                       29

<210> SEQ ID NO 3
<211> LENGTH: 21
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 3
agaaacaaac aaacaaacaa a                                               21

<210> SEQ ID NO 4
<211> LENGTH: 72
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 4
cctttcagga cgatgcttcg gtgccttaag acacctacct ttgtgtctat gacatgtgag    60
```
cccaacagtg gc                                                              72

<210> SEQ ID NO 5
<211> LENGTH: 26
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 5
cccgtctagg cgttcggtgt ccggcc                                               26

<210> SEQ ID NO 6
<211> LENGTH: 12
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 6
caggagcctc ga                                                              12

<210> SEQ ID NO 7
<211> LENGTH: 24
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 7
tcagccagtt ccaccccgtg cacg                                                 24

<210> SEQ ID NO 8
<211> LENGTH: 18
<212> TYPE: DNA
<213> ORGANISM: Artificial Sequence
<220> FEATURE:
<223> OTHER INFORMATION: sequence element of a nucleic acid molecule
      with a caryopsis-specific promoter

<400> SEQUENCE: 8
atactctggt catgttaa                                                        18

<210> SEQ ID NO 9
<211> LENGTH: 20
<212> TYPE: DNA
<213> ORGANISM: Artificial Sequence
<220> FEATURE:
<223> OTHER INFORMATION: primer used in PCR reaction, obtained from
      Roche Diagnostics GmbH, Manheim, Germany

<400> SEQUENCE: 9
atggcggctc tggtcacgtc                                                      20

<210> SEQ ID NO 10
<211> LENGTH: 20
<212> TYPE: DNA
<213> ORGANISM: Artificial Sequence
<220> FEATURE:
<223> OTHER INFORMATION: primer used in PCR reaction, obtained from
      Roche Diagnostics GmbH, Manheim, Germany

<400> SEQUENCE: 10

```
aggccgccag tcttgctcca                                              20

<210> SEQ ID NO 11
<211> LENGTH: 13
<212> TYPE: DNA
<213> ORGANISM: Triticum aestivum

<400> SEQUENCE: 11
ccacacacta caa                                                     13
```